United States Patent [19]
Vincent et al.

[11] Patent Number: 5,824,772
[45] Date of Patent: *Oct. 20, 1998

[54] FLUORESCENT SOMATOSTATIN

[75] Inventors: Jean-Pierre Vincent, Cagnes sur Mer; Georges Gaudriault, Nice, both of France; Alain Beaudet, Mount Royal, Canada

[73] Assignee: Advanced Bioconcept, Inc., Montreal, Canada

[*] Notice: The term of this patent shall not extend beyond the expiration date of Pat. No. 5,693,679.

[21] Appl. No.: 475,751

[22] Filed: Jun. 7, 1995

Related U.S. Application Data

[63] Continuation-in-part of Ser. No. 416,007, Apr. 4, 1995, Pat. No. 5,693,679.

[51] Int. Cl.$^6$ .................................................. C07K 15/00
[52] U.S. Cl. .......................................... 530/311; 435/7.1
[58] Field of Search .............................. 530/311; 435/7.1

[56] References Cited

U.S. PATENT DOCUMENTS

| | | | |
|---|---|---|---|
| 4,046,633 | 9/1977 | Keutel | 195/103.5 R |
| 4,145,337 | 3/1979 | Dairman et al. | 260/112.55 |
| 5,274,113 | 12/1993 | Kang et al. | 548/405 |
| 5,552,520 | 9/1996 | Kim et al. | 530/311 |

FOREIGN PATENT DOCUMENTS

| | | |
|---|---|---|
| 0 331 126 A2 | 9/1989 | European Pat. Off. . |
| 0 466 565 A1 | 1/1992 | European Pat. Off. . |
| 0 606 804 | 7/1994 | European Pat. Off. . |
| 0606804 | 7/1994 | European Pat. Off. . |
| 606804 A2 | 7/1994 | European Pat. Off. . |
| 0 608 987 | 8/1994 | European Pat. Off. . |
| 27 02 699 A1 | 12/1977 | Germany . |
| WO 93/04194 | 3/1993 | WIPO . |
| WO 93/18068 | 9/1993 | WIPO . |
| WO 95/22341 | 8/1995 | WIPO . |

OTHER PUBLICATIONS

Beaudet et al., "Neuropeptide Internalization in the Central Nervous System Applied to the Study of . . . " Annales d'endocrinologie, p. L14, Sep. 1–3, 1994, (conference date not published date).

Beaudet et al., "Internalization and Intracellular Mobilization of Neurotensin in Neuronal Cells", Biochemical Pharmacology, 47:43–52, 1994.

Bechtol et al., "Using Dyes and Filters in a Fluorescent Imaging System", American Biotechnology Laboratory, 8–10, 1994.

Bunnett et al., "Characterization of Receptors Using Cyanine 3–Labeled Neuropeptides", Peptides, 16:733–740 1995.

Cheng et al., "Receptor–Meditated Uptake of 3,3', 5–Triiodo–L–Thyronine by Cultured Fibroblasts", Proc. Natl. Acad. Sci. USA, 77:3425–3429, 1980.

Chersi et al., "Preparation and Utilization of Fluorescent Synthetic Peptides", Barhimica et Biophysica Acta. 1034:333–336, 1990.

Epelbaum, "Somatostatin Receptors in the Central Nervous System", Somatostain, 17–28, 1992.

Garland et al., "Agonist–Induced Internalization of the Substance P ($NK_1$) Receptor Expressed in Epithelial Cells", Biochem, J., 303:177–186, 1994.

Grady et al., "Delineation of the Endocytic Pathway of Substance P and Its Seven–Transmembrane Domain NK1 Receptor", Molecular Biology of the Cell, 6:509–524, 1995.

Grady et al., "Direct Observation of Endocytosis of Gastin Releasing Peptide and Its Receptor", J. of Bio. Chem., 270:4603–4611, 1995.

Haugland, Handbook of Fluorescent Probes and Research Chemicals, 5th Edition, Molecular Probes, Inc., 5–8, 1992–1994.

Hazum et al., "Fluorescent and Photo–Affinity Enkephalin Derivatives: Preparation and Interaction with Opiate Receptors", Biochemical and Biophysical Research Communications, 88:841–846, 1979.

Jans et al., "Lateral Mobility of the Phospholipase C–Activating Vasopressin $V_1$–Type Receptor in A7r5 Smooth Muscle Cells: A Comparison With the Adenylate Cyclase–Coupled $V_2$–Receptor", EMBO Journal, 9:2693–2699, 1990.

Maton et al., "Therapeutic Use of Somatostain and Octreotide Acetate in Neuroendocrine Tumors", Somatostatin, 4:55–66, 1992.

Maxfield, "Fluorescent Analogs of Peptides and Hormones", Methods in Cell Biology, 29:13–28, 1989.

Niedel et al., "Receptor–Mediated Internalization of Fluorescent Chemotactic Peptide by Human Neutrophils", Science, 205:1412–1414, 1979.

Rivier et al., "D–$Trp^8$–Somatostatin: An Analog of Somatostatin More Potent than the Native Molecule", Biochemical and Biophysical Research Communications, 65:746–751, 1975.

Schaffner et al., "Fluorescence–Activated Cell Sorting of Embryonic Mouse and Rat Motoneurons and Their Long–Term Survival in vitro", J. of Neuroscience, 7:3088–3104, 1987.

(List continued on next page.)

*Primary Examiner*—Cecilia J. Tsang
*Assistant Examiner*—C. Delacroix-Muirheid
*Attorney, Agent, or Firm*—Clark & Elbing LLP

[57] ABSTRACT

Light-emitting compounds of the formula:

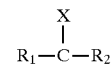

where $R_1$ is a light-emitting moiety and $R_2$ is a somatostatin-based peptide featuring a first amino acid sequence -Phe-Phe-Trp-Lys-Thr- or (SEQ ID NO:1) or -Phe-Phe-D-Trp-Lys-Thr-. The peptide is linked at a first amino acid position to (C-X), and the light-emitting compound exhibits substantial biological activity in the presence of a receptor having affinity for somatostatin-based peptides.

21 Claims, 4 Drawing Sheets

OTHER PUBLICATIONS

Scicchitano et al., "Distribution of Somastatin Receptors on Murine Spleen and Peyer's Patch T and B Lymphocytes", Brain, Behavior, and Immunity, 1:173–184, 1987.

Taylor et al., "Fluorescently Labelled Molecules as Probes of the Structure and Function of Living Cells", Nature, 284:405–410, 1980.

Varga et al., "Association of Cell Surface Receptors for Melanotropin With the Golgi Region in Mouse Melanoma Cells", Proc. Natl. Acad. Sci. USA, 73:559–562, 1976.

Walker et al., "High Level Expression of Human Neuropeptide Y Receptors in Mammalian Cells Infected With a Recombinant Vaccinia Virus", Molecular and Cellular Endocrinology, 91:107–112, 1993.

Yamada et al., "Cloning and Functional Characterization of a Family of Human and Mouse Somatostatin Receptors Expressed in Brain, Gastrointestinal Tract, and Kidney", Proc. Nat. Acad. Sci. USA, 89:251–255, 1992.

Scicchitano et al., "Distribution of Somatostatin Receptors . . . ", *Brain, Behavior, and Immunity*, 1:173–184, 1987.

Rivier et al., "D–Trp$^8$–Somatostatin . . . " *Biochemical and Biophysical Research Commun*, 65:746–751, 1987.

Zhao, "Attachment of a single fluorescent label to peptides for determination by capillary zone electrophoresis" Journal of Chromatography, 608:239–242,1992.

FLUORESCENT SOMATOSTATIN

This application is a continuation-in-part of U.S. Ser. No. 08/416,007, entitled "Fluorescent Somatostatin", filed Apr. 4, 1995 now U.S. Pat. No. 5,695,679.

BACKGROUND

This invention relates to light-emitting peptide compounds.

Peptides may be complexed with detectable "labels" and used, for example, to monitor peptide, cytokine, drug, and hormone receptors at the cellular level. In a typical application, the labelled peptide is placed in contact with a tissue or cell culture to facilitate binding to an available receptor. Once bound, the label can then be detected, allowing properties such as receptor distribution or receptor binding kinetics to be monitored.

Peptides are typically labelled with radioactive elements such as $^{125}I$ or $^3H$. In this case, emission of high-energy radioactive particles is monitored using standard γ-ray detectors, thereby allowing detection of the label. While detection techniques for $^{125}I$ and $^3H$ are well-known, radioactive compounds by nature have limited half lives, and are often both toxic and expensive. Moreover, current detection technology makes it difficult or impossible to detect radioactive probes in real-time, thereby precluding study of kinetic processes.

Somatostatin is a particularly desirable peptide to label and use to monitor cell receptors, as this compound exhibits biological activity in a number of organs, such as the brain, pituitary and endocrine systems, and the kidneys. In particular, somatostatin, when bound to an outer membrane receptor, appears to cause release of hormones and secretory proteins capable of inducing multiple physiological effects (Yamada et al., Proc. Nat. Acad. Sci., Biochemistry, Vol. 89, p. 251–255 (1992)). Somatostatin is synthesized in the hypothalamus and other regions, has a cyclical configuration, and exists naturally as either a 14-residue (i.e., somatostatin-14) or 28-residue (i.e., somatostatin-28) peptide. Both forms share the same 14 amino acids at the carboxy terminus, have similar affinities for the same receptor, and appear to be equally potent in producing a biological response (Maton et al., "Basic and Clinical Aspects of Neuroscience", Springer Sandoz Advanced Texts, Vol. 4, pp 55–63 (1985)).

SUMMARY

In general, in one aspect, the invention provides a compound of the formula:

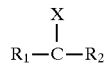

where $R_1$ is a light-emitting moiety and $R_2$ is a complex Y-Z-Q having binding affinity for a somatostatin receptor. In particular, in $R_2$, each Y and Q, independently, is a chain of between 1 to 40 amino acids, inclusive, and Z contains -Phe-Phe-Trp-Lys-Thr- (SEQ ID NO:1) or -Phe-Phe-D-Trp-Lys-Thr-. X is =O, =S, —OH, =C=O, =NH, —H, —OR, —NR, —R, or —$R_6R_3R_4$, wherein each R, $R_6$, $R_4$, $R_3$, independently, is H or a C1–C6 branched or unbranched, substituted or unsubstituted alkyl. C of X-C is bonded via an amino or thiol group to an amino acid (e.g., an -Ala- residue) of $R_2$. In this configuration, the compound, when compared to $R_2$ alone, retains at least 25% of its binding affinity for the human somatostatin receptor in vivo. Preferably, the compound is in the form of a pharmaceutically acceptable salt or complex thereof.

In preferred embodiments, $R_2$ is a somatostatin-based peptide, and either -Phe-Phe-Trp-Lys-Thr- (SEQ ID NO:1) or -Phe-Phe-D-Trp-Lys-Thr- is located in the peptide at positions 7–11. Here, by "somatostatin-based peptide" is meant a peptide which includes somatostatin, fragments of somatostatin, or derivatives thereof. Somatostatin-based peptides may be peptides whose sequences differ from somatostatin's wild-type sequence by only conservative amino acid substitutions. For example, one amino acid may be substituted for another with similar characteristics (e.g., valine for glycine, arginine for lysine, etc.) or by one or more non-conservative amino acid substitutions, deletions, or insertions which do not abolish the peptide's biological activity. Other useful modifications include those which increase somatostatin's stability. The peptide may contain, for example, one or more non-peptide bonds (which replace a corresponding peptide bond) or D-amino acids in the peptide sequence. In particular examples, the somatostatin-based peptides may be somatostatin-14 or D-Trp$^8$-somatostatin-14.

In some embodiments, the N-terminus of the somatostatin-based peptide described above contains -Ala-Gly-Cys-Lys-Asn-Phe- (SEQ ID NO:2). In other embodiments, the peptide's C-terminus contains -Phe-Thr-Ser-Cys- (SEQ ID NO:3). In still other embodiments, the peptide contains both -Ala-Gly-Cys-Lys-Asn-Phe- (SEQ ID NO:2) and -Phe-Thr-Ser-Cys-. These sequences, for example, are present in somatotstatin-based peptides such as somatostatin-14 or D-Trp$^8$-somatostatin-14.

The light-emitting moiety attached to the compound can be any moiety which emits an optical field following excitation. Preferably, the moiety is selected from the group consisting of Bodipy, fluorescein, FTC, Texas red, phycoerythrin, rhodamine, carboxytetra-methylrhodamine, DAPI, indopyras dyes, Cascade blue, coumarins, NBD, Lucifer Yellow, propidium iodide, and derivatives thereof. Other light-emitting complexes used in labelling or other applications may be attached to the compound in place of the above moieties.

In another aspect, the invention provides a compound having the chemical substituents described above which is selected from secondary compounds having relatively low biological activities. The selection can be accomplished by exposing the compound to a receptor recognizing a somatostatin-based peptide, and then selectively isolating the exposed compound if the compound exhibits substantial biological activity. Here, "substantial biological activity" is meant the compound preferably binds to a receptor having an affinity for a labelled somatostatin-based peptide which is at least 0.25% of that of the corresponding unlabelled somatostatin-based peptide. More preferably, the receptor affinity for the labelled somatostatin-based peptide is at least 1.0% of that of the corresponding unlabelled somatostatin-based peptide. Receptor affinity in this case can be determined using known methods, such as by measuring the $K_d$ for the receptor/peptide interaction. For example, a compound having substantial biological activity can be selected using high-pressure liquid chromatography.

The invention has many advantages. In a general sense, compounds containing light-emitting dyes rather than radioactive labels are advantageous during processes involving their synthesis, detection, and disposal. For example, when compared to radiolabelled compounds, fluorescent somatostatin is relatively safe and non-toxic, thereby allowing it to be synthesized and used without employing special laboratory procedures. Following use, fluorescent somatostatin may be easily disposed, whereas disposal of radioactive compounds is both time-consuming and costly. In addition, fluorescent markers for somatostatin receptors are stable and may be stored for extensive periods of time, while radioactive markers by nature undergo radioactive decay and thus have a limited lifetime (for example, the half-life for $^{125}$I is 60 days).

Use of somatostatin in the labelled compound is also advantageous. As described above, somatostatin exhibits biological activity in organs such as the brain, pituitary and endocrine systems, and the kidneys, and can therefore be used as a probe to investigate a large number of different cell types. In addition, this peptide has a relatively simple structure (14 amino acids) and can be synthesized and isolated with standard, well-known techniques.

During typical experiments, fluorescent markers for somatostatin receptors emit optical signals, and thus may be monitored by eye or with the aid of external optical detectors. In this way, the fluorescent peptides obviate the need for secondary detection steps sometimes used for radiolabelled compounds; for instance, the compounds of the invention do not have to be incubated with secondary labeled compounds. Detection of optical radiation is, in general, relatively simple and cost-effective compared to detection of radioactive particles (e.g., γ particles); conventional CCDs or light-sensitive cameras can therefore be used without modification for this application.

In addition, because of their high optical emission rates and well-characterized emission cross sections, fluorescent markers attached to somatostatin receptors can be used for real-time, quantified imaging of a number of dynamic biological phenomena, such as kinetics associated with receptor binding. The compounds can also be used for static processes, such as monitoring peptide distribution within a cell. Somatostatin receptors marked with fluorescent peptides may also be used in flow cytometry, cell sorting, confocal microscopy, fluorescence polarization spectroscopy, and any other techniques exploiting the optical detection of fluorescence or photoluminescence.

Other advantages and features of the invention will become apparent from the following detailed description, and from the claims.

DETAILED DESCRIPTION

Figure 1:
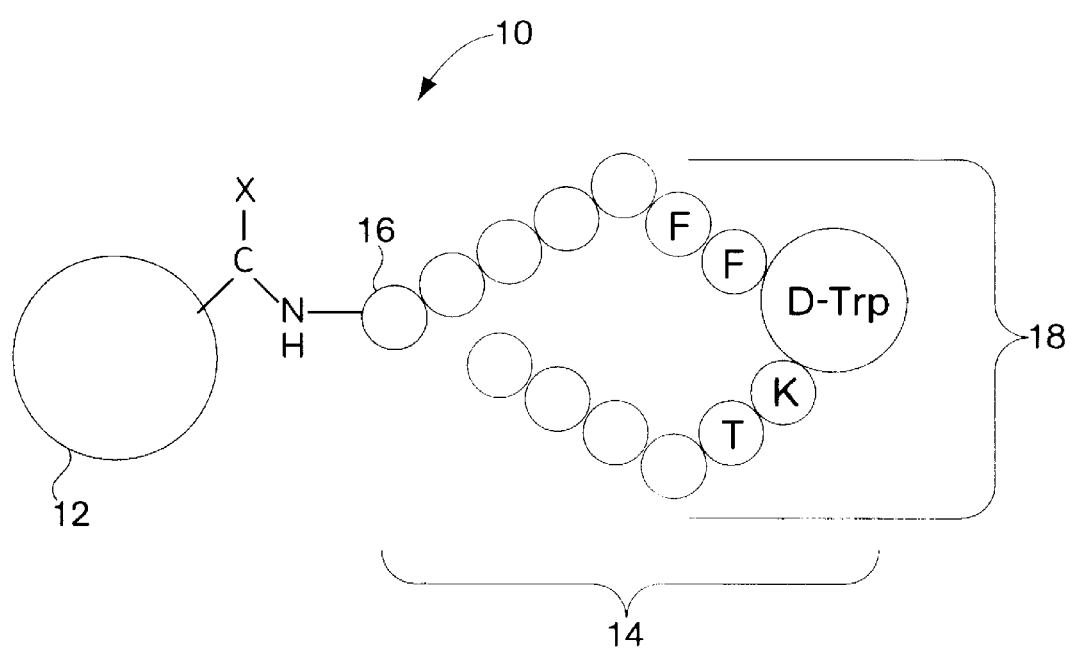
FIG. 1 is a somewhat schematic drawing of the chemical structure of fluorescent peptides according to the invention.

Referring first to FIG. 1, in a preferred embodiment, a fluorescent peptide 10 according to the invention includes a light-emitting moiety 12, such as a fluorescent dye, linked via a —(CX)— bond to a peptide moiety 14. The peptide moiety 14 includes amino acid residues at the 7–11 positions of the somatostatin peptide, which itself is composed of the following sequence: -Ala-Gly-Cys-Lys-Asn-Phe-Phe-Trp-Lys-Thr-Phe-Thr-Ser-Cys- (SEQ ID NO:4). Thus, as indicated in the figure by the region 18, the peptide moieties include amino acids -Phe-Trp-Lys-Thr-Phe- (SEQ ID NO:5). In a more general sense, the peptide moiety can be formulated as Y-Z-Q, where each Y and Q, independently, is a chain of between 1 to 40 amino acids, inclusive, and Z contains -Phe-Phe-Trp-Lys-Thr- (SEQ ID NO: 1) or -Phe-Phe-D-Trp-Lys-Thr-.

In order to retain substantial biological activity and affinity for somatostatin receptors, the peptide moiety is attached to the —(CX)— bond at the first amino acid residue (indicated by the region 16) at the N-terminus. For example, in a preferred embodiment, the peptide moiety is attached via a Nα-Ala1 bond to an acyl group. The light-emitting moiety, in turn, is preferably covalently linked at any available position to the —(CX)— bond. This bond can include groups such as C=O, C=S, CH(OH), C=C=O, C=NH, CH$_2$, CHOH, CHOR, CNR, CH—R, C—R$_6$R$_3$R$_4$, wherein each R, R$_6$, R$_4$, R$_3$, independently, is H or a C1–C6 branched or unbranched, substituted or unsubstituted alkyl.

Fluorescent peptides of this type have amino acids which are available for binding to somatostatin-recognizing receptors, thereby enabling the peptide to be used for labelling purposes. Once bound to an available receptor, the attached light-emitting moiety retains optical properties similar to those of the un-bound light-emitting molecule. In this way, the fluorescent peptide can bind to the corresponding receptor and emit light following absorption of an incident optical field, and thus serve as a marker for the somatostatin receptor. This allows the receptor to be "labelled" and permits investigation, for example, of peptide/receptor interactions. In particular, labelled peptides participating in receptor/peptide interactions can be monitored to determine the location of receptors in cell or tissue samples, and additionally allow quantification of receptors, determination of the receptor affinity for various ligands, or the identification of various populations of cells.

Somatostatin-based peptides may be synthesized using techniques known in the art, extracted from natural systems, or obtained from commercial sources (e.g., Peninsula, Neosystems, Sigma, and BASF). A list of somatostatin analogs which may be used is described, for example, in "Somatostatin", Weil, Muller, and Thorner (eds.), (1992), the contents of which are incorporated herein by reference. Of particular relevance is the chapter "Somatostatin Receptors in the Central Nervous System", by J. Epelbaum. Typically, the peptide is either purchased or synthesized using conventional solid-phase synthetic techniques. Preferably, the peptide is substantially pure, meaning that it is at least 60% by weight free from the other compounds with which it is naturally associated.

In general, any dye, porphyrin, fluorophore, or other light-emitting compound may be complexed with the somatostatin-based peptide. As described above, in preferred embodiments, the light-emitting moiety is selected from the group including Bodipy, fluorescein, FTC, Texas red, phycoerythrin, rhodamine, carboxytetramethylrhodamine, DAPI, indopyras dyes, Cascade blue, coumarins, NBD, Lucifer Yellow, propidium iodide, and derivatives thereof. The synthesis and structures of several dyes which may be used are described in U.S. Pat. Nos. 5,248,782; 5,274,113; and, 5,187,288, the contents of which are incorporated herein by reference.

Once the desired peptide is obtained, fluorescent peptides having high biological activities are made by attaching the light-emitting moiety to the first amino acid position of the somatostatin-based moiety. In general, this reaction is carried out by modifying a functional group on the peptide, most typically a thiol or amine group, so that this moiety may be easily attached to the light-emitting compound. Reactions for such modifications are described in, for example, "Handbook of Fluorescent Probes and Research Chemicals—5th Edition" by Richard P. Haugland (1992), the contents of which are incorporated herein by reference. In general, thiols react with alkylating groups (R'—X) to yield relatively stable thiol ethers (R—S—R'), with the leaving group X preferably being a halogen (e.g., Cl, Br, I) or similar leaving group. In particular, the most common reagents for derivatization of thiols are haloacetyl derivatives. Reaction of these reagents with thiols proceeds rapidly at or below room temperature in the physiological pH range. The general chemical properties of the dyes used in the fluorescent peptides shown in FIGS. 2A and 2B (i.e., succinimidyl esters) are, for example, described in "Set 5" on page 6 of this manual.

The conditions used to modify amine moieties of the desired peptide will depend on the class of amine (e.g., aromatic, aliphatic) and its basicity. Aliphatic amines, such as the α-amino group of lysine, are moderately basic and reactive with acylating reagents. The concentration of the free base form of aliphatic amines below pH 8 is very low; thus, the kinetics of acylation reactions of amines by isothiocyanates, succinimidyl esters, and other reagents is strongly pH-dependent. Although amine acylation reactions should usually be carried out above pH 8.5, the acylation reagents degrade in the presence of water, with the rate increasing as the pH increases. Therefore, a pH of 8.5–9.5 is usually optimal for modifying lysines. The α-amino function of the amino terminus usually has a $pK_a$ of ~7, thereby allowing it to be selectively modified by reaction at neutral pH.

In general, reactive groups on the light-emitting moiety, such as unsaturated alkyl groups, will react with the modified peptide to form a dye/peptide bond. The chemical structure of the light-emitting moiety may affect the synthetic route used to synthesize the fluorescent somatostatin analog. It may be necessary, for example, to modify the light-emitting moiety so that it includes a reactive group prior to exposing this moiety to the desired peptide.

The chemistry used to synthesize the fluorescent peptide does not vary significantly depending on the exact structure of the somatostatin analog. Thus, the general procedure outline below may be used for most somatostatin-based peptides. Moreover, derivatives of somatostatin have been found to be especially biologically active, and may be used in the fluorescent peptides described herein to label somatostatin receptors. For example, a preferred compound is the analog D-Trp$^8$-somatostatin 14 (Ala-Gly-Cys-Lys-Asn-Phe-Phe-D-Trp-Lys-Thr-Phe-Thr-Ser-Cys (SEQ ID NO:4) which is about eight times more potent than somatostatin, most probably due to this compound's enhanced resistance to enzymatic degradation. (Rivier et al., Biochem. and Biophys. Res. Comm. Vol. 65, No.2, pp 746–751 (1975)). Attachment of this peptide to a light-emitting moiety is described in detail in the Examples provided below.

Once synthesized, the resulting complex is purified, preferably using a column method such as HPLC, and then eluted. Collected fractions are then screened using analytical methods, such as HPLC, to determine if adequate biological activity is present. Fluorescent somatostatin analogs having adequate biological activities are selected by first exposing these analogs to somatostatin receptors; compounds binding effectively to these sites are then isolated from relatively inactive fluorescent peptides. In general, this selection process can be performed using standard techniques, such a column chromatography or other analytical techniques known in the art. The selection process is designed to allow maintenance of the compound's pharmacological binding, and thus allows only the dye/peptide compounds exhibiting substantial biological activities to be separated from relatively inactive compounds.

Figure 2A:
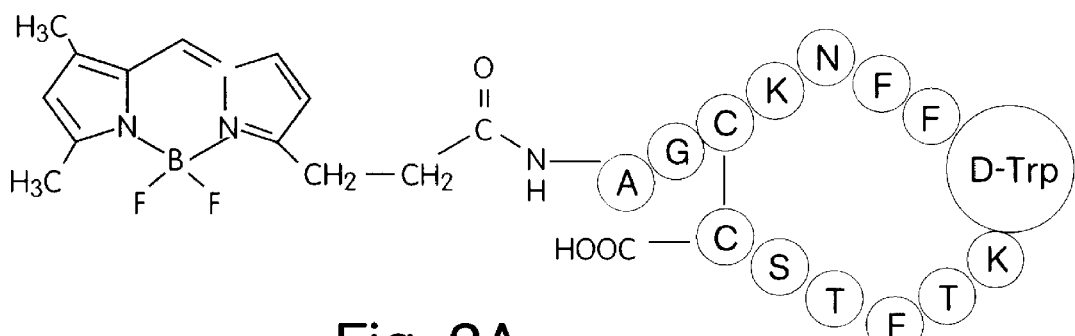
FIGS. 2A and 2B are somewhat schematic drawings of the chemical structures of, respectively, Bodipy-labelled D-Trp$^8$ somatostatin and fluorescein-labelled D-Trp$^8$ somatostatin.
Figure 2B:
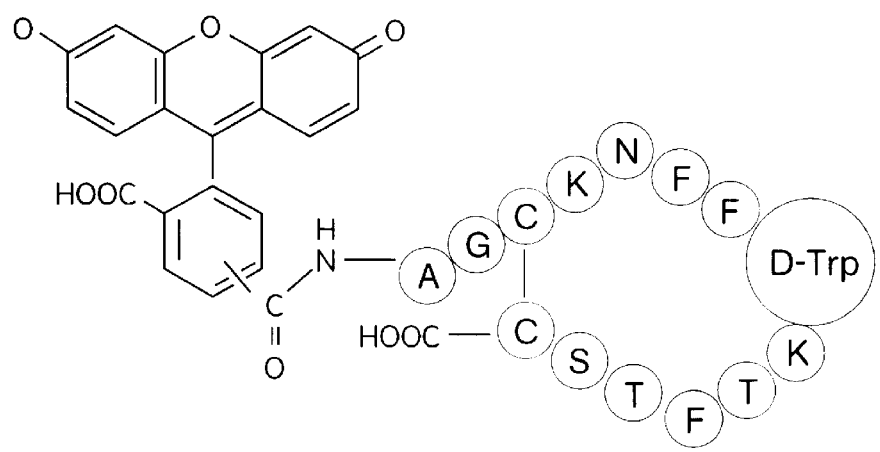

Referring now to FIGS. 2A and 2B, in preferred embodiments, the light-emitting moiety is attached via an amide moiety to a somatostatin analog containing a D-tryptophan residue at the 8 position. In this case, the peptide has the structure -Ala-Gly-Cys-Lys-Asn-Phe-Phe-D-Trp-Lys-Thr-Phe-Thr-Ser-Cys- and is attached to an amino acid residue at the 1 position to the amide linkage which, in turn, is covalently bonded to a linear (FIG. 2A) or cyclical (FIG. 2B) alkyl group of the light-emitting moiety. The compound shown in FIG. 2B, Nα-fluoresceinyl [D-Trp$^8$]somatostatin-14, absorbs light in the range of 442–488 nm and features an emission spectrum centered around 530–546 nm. The synthesis of a compound having a similar stucture is described in detail in the Examples provided below. The compound shown in FIG. 2A, Nα-Bodipy[D-Trp$^8$] somatostatin-14, absorbs light in the range of 460–488 and emits light at wavelengths centered around 530 nm. Like fluorescein, Bodipy is a succinimidyl ester, and thus synthesis of this compound is similar to that described in the Examples, with the appropriate steps being used to attach the amide linkage to the Bodipy's unsaturated ring structure.

Figure 3:
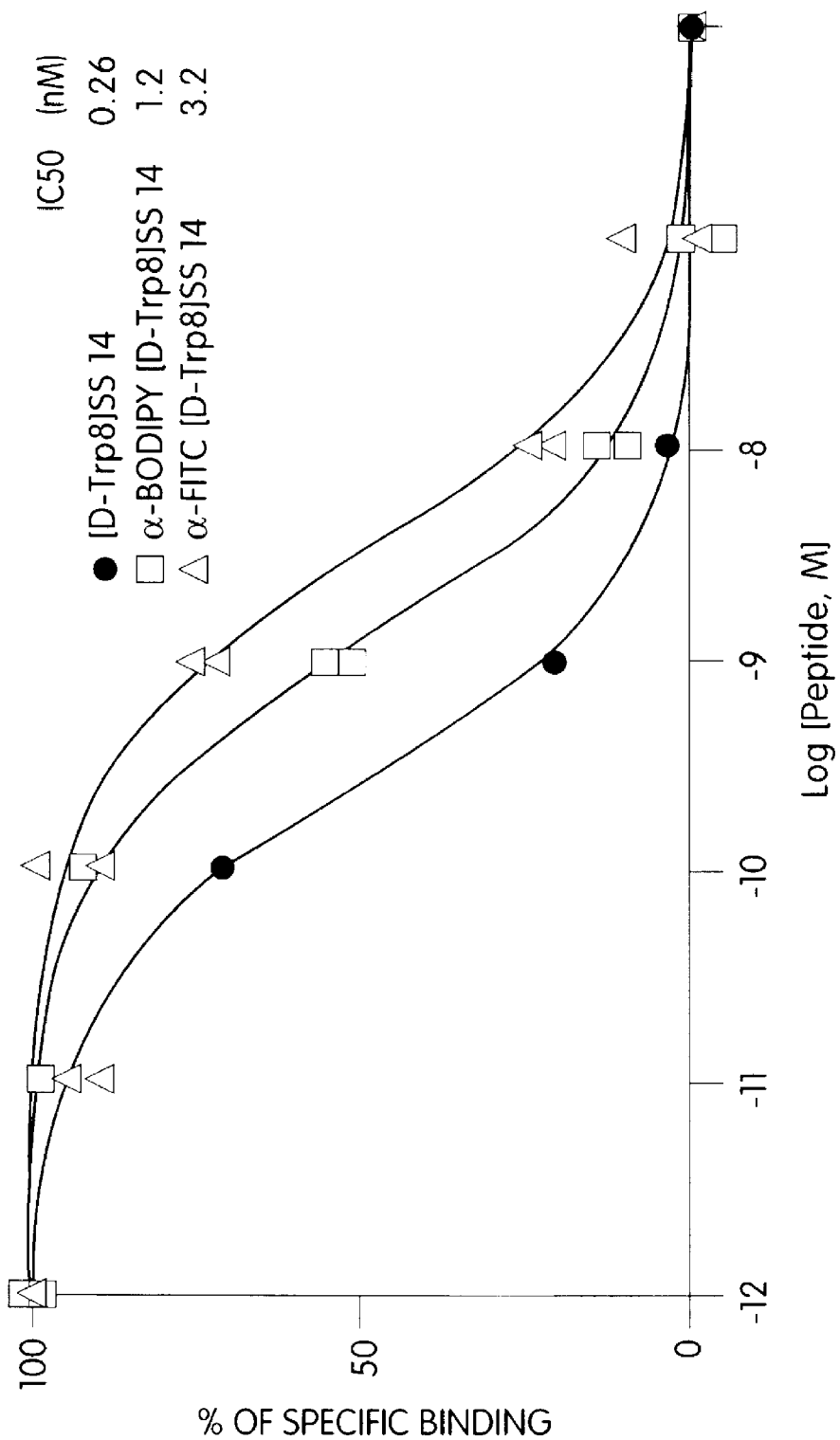
FIG. 3 is a plot showing the amount of specific binding of the invention's fluorescent peptides as a function of their concentration.

Referring now to FIG. 3, fluorescent peptides having the chemical structure shown in FIGS. 2A and 2B exhibit comparable, dose-dependent binding to somatostatin receptors when compared to radiolabelled somatostatin peptides. The graph shows the binding of fluorescein and Bodipy-labelled [D-Trp$^8$] somatostatin-14 as determined by percent inhibition of the binding of [$^{125}$I-Tyr$^{11}$] somatostatin 14 to somatostatin receptors. The concentrations at which 50% of the binding is inhibited (i.e., the IC$_{50}$) is 1.2 nM for the Bodipy-labelled compound, and 3.2 nM for the fluorescein-labelled compound, as compared to 0.26 nM for the unlabelled somatostatin.

Fluorescent somatostatin compounds selected to have high biological activities can be used in a number of applications. During most applications, the fluorescent somatostatin compound is first contacted with the sample of interest. The labelled analog is then incubated with the cell or tissue culture for a select time period and allowed to interact with the somatostatin receptor; if necessary, excess, non-specifically bound somatostatin is washed away.

Once bound to the desired receptor sites, the labelled sample is imaged using standard techniques known in the art. In this way, small-scale features in the cell which normally would be difficult or impossible to detect may be imaged. For example, this allows visualization of intracellular receptor sites. Conventional microscopy methods, such as fluorescence or confocal microscopy, may then be used to optically excite and then detect emission from the labelled receptors. Other imaging techniques which can be used with the fluorescent somatostatin-based peptides include atomic force microscopy, fluorescence polarization spectroscopy, and fluorimetry.

Because the labelled peptides, once excited, emit optical radiation, standard optical detectors can be used during the imaging process. For example, detectors such as charge-coupled devices (CCDs), diode arrays, video cameras, or any other light-sensitive detector can be used in combination with the magnifying and optical imaging systems described above.

Optical radiation emitted from the fluorescing moiety can be easily and rapidly detected, allowing the fluorescent peptides to be used to monitor real-time receptor/peptide interactions. In this way, the compounds permit study of kinetic processes in the cell. Other techniques which can use to advantage the labelled somatostatin peptides include flow cytometry, cell sorting, tumor marking, competitive binding assays for drug screening, fluorescent immunoassays, and other in vitro experiments involving compound labelling according to techniques known in the art.

The following Examples are used to more particularly point out the synthesis, selection methods, and use of fluorescent somatostatin analogs having high biological activities.

EXAMPLES

1. Fluorescent labeling of D-Trp$^8$-somatostatin

1mmole NHS FTC (an isothiocyanate analog of fluorescein; Molecular Probes) was first diluted in 200 ml of acetonitrile (Pierce) and then incubated with D-Trp$^8$-ss1–14 (0.6 mmole; Neosystems) in a final volume of 1 ml Borate/Phosphate Buffer (50 mM/50 mM) at pH 6.5 for 3 hours at 4° C. The solution was purified on an HPLC C18 column (10 mm×250 mm, Ultrosphere, ODS, Beckmann Instruments) and eluted in 0.1% TFA with a linear gradient of acetonitrile from 20% to 70% during 100 minutes at a debit rate of 1 ml/min. Elution of the compound was monitored by observing optical density profiles at 213 nm.

Collected fractions were screened by analytical HPLC using both UV and fluorescence detection, with the excitation wavelength being 338 nm, and the emission wavelength at 425 nm, and then lyophilized.

Once synthesized, fluorescent peaks were monitored, with the compound then being subjected to Edman's degradation to determine whether the α amino function present on the amino terminal amino acid was free or blocked. The first and largest peak was found to be unchanged when the compound was exposed to phenylisothiocyanate, and therefore corresponded to FTC-[Ala$^1$]-D-Trp$^8$-ss. The amino acid composition of this fragment was assessed by quantitative amino acid analysis after acidic hydrolysis in vacuo (6N HCl, 110° C., 18 h) and carboxypeptidase Y digestion (6U/0.3 mmole, 37° C., 48 h).

The site of attachment between the NHS fluorescein and the somatostatin analogue was confirmed to be at the N-terminus, and was identified as Nα-Ala1. Isolation of this peak yielded a compound with a molar ratio of NHS fluorescein to D-Trp$^8$-somatostatin of 1:1. FTC-[Ala$^1$-]-D-Trp$^8$-somatostatin was evaluated to be pure as indicated by a single elution peak from reverse phase HPLC. The compound was freely soluble in water or aqueous buffer, and was stable if protected from light and maintained in a lyophilized form at 4° C.

2. Pharmacological Binding

Competition studies were carried out with radiolabelled peptides to test the receptor-binding efficacy of FTC-[Ala$^1$-1]-D-Trp$^8$-somatostatin. Here, the competition studies using the fluorescent peptide and $^{125}$I somatostatin were performed on purified rat brain membranes according to well-known methods known in the art. Membranes were incubated with 0.1 nM of radiolabeled somatostatin in the presence of varying concentrations of FTC-[Ala$^1$]-D-Trp$^8$-somatostatin in 50 mM Tris HCl pH 7.5 containing 0.2% bovine serum albumin. The reaction was carried out for 20 minutes at 22° C. and stopped by addition of ice-cold buffer. Membranes were then subjected to immediate filtration over Gelman™ filters (Millipore™) under vacuum. They were then washed and their radioactivity concentration measured using a standard gamma counter (LKB, Inc.).

Data are expressed as the percentage of specific binding of the radioligand in the absence of fluorescent competitor. IC$_{50}$ values were obtained from plotting individual values using the EBDA/Ligand program. Referring again to FIG. 3, the fluorescent analogue of somatostatin displaced the specific $^{125}$I-somatostatin binding in a dose-dependent manner. The IC$_{50}$ value for unlabeled D-Trp$^8$-somatostatin was 0.26 rM; the corresponding value for FTC-[Ala$^1$]-D-Trp$^8$ somatostatin was 3.2 nM.

Figure 4:
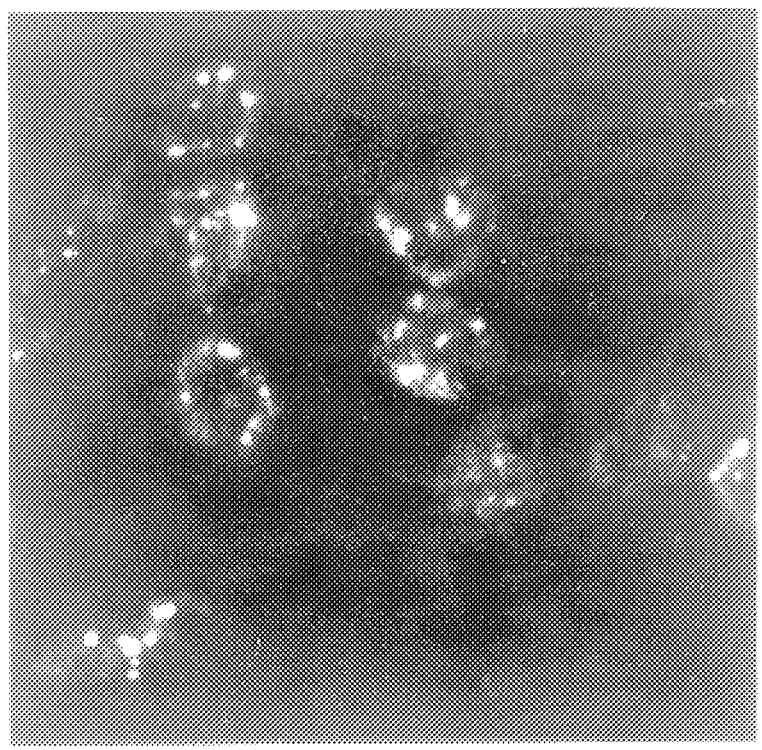
FIG. 4 is a photograph showing a Chinese hamster ovary cell containing receptors labelled with fluorescein-labelled somatostatin.

3. Confocal microscopic visualization of somatostatin receptors: Internalization of FTC-[D-Trp$^8$] somatostatin in CHO cells expressing sstr1 or sstr2 a receptors Cells incubated with the fluorescent peptide were monitored using standard confocal microscopy methods to determine the locations of somatostatin-recognizing receptors. The microscope used was manufactured by Leica. Referring now to FIG. 4, in these experiments, incubation of Chinese hamster ovary (CHO) cells stably transfected with cDNA encoding sstr1 or sstr2 somatostatin receptor sub-types with 10 nM FTC-labelled somatostatin for 45 minutes at 37° C. resulted in an intense fluorescent labeling of the CHO cells. The presence of light-emitting portions of the cells, monitored using serial confocal microscopic optical sectioning, revealed that labelling was intracytoplasmic and in the form of small endosome-like particles. In both types of transfected cells, the sizes of these fluorescent particles were found to increase with time, while the number of particles decreased with time; this suggests a fusion of the endocytic compartments.

Internalization of FTC-labelled somatostatin was prevented by carrying out the incubation at 4° C. or, alternatively, in the presence of the endocytosis inhibitor phenylarsine oxide, thereby indicating that the internalization process was endocytic in nature. In both conditions, labeling remained confined to the cell surface as confirmed by confocal microscopic optical sectioning and by the fact that the labeling was totally abolished by a two-minute wash in acid solution (pH 4).

Somatostatin internalization proved to be receptor-dependent, as demonstrated by the lack of either surface labeling (at 4° C.) or intracytoplasmic labeling (at 37° C.) when the experiments were carried out in the presence of a thousand-fold excess of non-fluorescent [D-Trp$^8$]-somatostatin.

4. Confocal microscopic visualization of somatostatin receptors: Internalization of α-BODIPY-somatostatin and FTC-somatostatin in COS cells expressing sstr1 or sstr2 a receptors Incubation of COS cells transiently transfected with cDNA encoding sstr1 or sstr2 somatostatin receptor sub-types with 5 nM of either α-Bodipy[D-Trp$^8$] somatostatin resulted in an intense fluorescent labeling of the cells. Approximately 50% of the cells were labelled with fluorescent somatostatin, and thus corresponded to those cells expressing somatostatin receptors (as verified by labelling with antibodies raised against somatostatin receptors). Serial confocal microscopic optical sectioning revealed that this labeling was intracytoplasmic and in the form of endosome-like particles.

Internalization of fluorescent somatostatin was prevented by concomitant incubation with the endocytosis inhibitor, phenylarsine oxide, in which case the labeling remained confined to the cell surface. Binding and internalization of both ligands were totally prevented when the incubation was carried out in the presence of a thousand-fold excess of non-fluorescent [D-Trp$^8$] somatostatin.

5. Internalization of α-Bodipy-[D-Trp$^8$] somatostatin-14 and α-FTC-[D-Trp$^8$] somatostatin-14 in slices of rat hypothalamus Superfusion of rat brain slices with 2–20 nM of either α-FTC-labelled somatostatin or α-Bodipy-labelled somatostatin for 45 minutes at 37° C. resulted in selective labeling of neuronal perikarya and dendrites dispersed across several brain regions. Labeling observed with either ligand was no longer apparent when the incubation was carried out at 4° C. or in the presence of a thousand-fold excess of non-fluorescent [D-Trp$^8$] somatostatin.

In the arcuate nucleus and lateral tuberal nucleus of the hypothalamus, the grouping of fluorescent somatostatin-labeled cells was reminiscent of that of neurons previously found to bind and express somatostatin receptors. At high magnification using the confocal microscope described above, the fluorescent signal took the form of small intensely fluorescent granules, suggesting an endocytotic compartmentalization of internalized ligand molecules comparable to that seen in transfected cell lines.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:1:

Phe  Phe  Trp  Lys  Thr
    1                        5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:2:

Ala  Gly  Cys  Lys  Asn  Phe
    1                        5

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:3:

Phe  Thr  Ser  Cys
    1

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: Not Relevant
        ( D ) TOPOLOGY: linear

```
      ( i i ) MOLECULE TYPE: protein ( x i ) SEQUENCE DESCRIPTION: SEQ ID NO:4:

Ala  Gly  Cys  Lys  Asn  Phe  Phe  Trp  Lys  Thr  Phe  Thr  Ser  Cys
         1                   5                        10

( 2 ) INFORMATION FOR SEQ ID NO:5:

( i ) SEQUENCE CHARACTERISTICS:
              ( A ) LENGTH: 5 amino acids
              ( B ) TYPE: amino acid
              ( C ) STRANDEDNESS: Not Relevant
              ( D ) TOPOLOGY: linear ( i i ) MOLECULE TYPE: protein ( x i ) SEQUENCE DESCRIPTION: SEQ ID NO:5:

Phe  Trp  Lys  Thr  Phe
         1                   5
```

Other embodiments are within the scope of the following claims.

What is claimed is:

1. A compound of the formula:

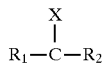

wherein $R_1$ is a light-emitting moiety;

$R_2$ is Y-Z-Q, wherein

Z comprises -Phe-Phe-Trp-Lys-Thr- (SEQ ID NO:1) or -Phe-Phe-D-Trp-Lys-Thr-; each of Y and Q is an amino acid sequence such that the number of amino acids in $R_2$ is between 7 and 28; and CX is C=O, C=S, —CHOH, C=C=O, C=NH, -CH$_2$, —CHOR, —C=NR, —CHR, —CR$_3$R$_4$, wherein each of R, R$_4$, and R$_3$, independently, is H or a $C_1$–$C_6$ branched or unbranched, substituted or unsubstituted alkyl; and C of X-C is bonded via an —NH— or —S— group to an amino acid of $R_2$; and wherein said compound, when compared to $R_2$ alone, retains at least 25% of its binding affinity for the human somatostatin receptor in vivo.

2. The compound of claim 1, wherein $R_2$ is a somatostatin-based peptide.

3. The compound of claim 2, wherein -Phe-Phe-Trp-Lys-Thr- (SEQ ID NO: 1) or -Phe-Phe-D-Trp-Lys-Thr- is located at positions 7–11 in said somatostatin-based peptide.

4. The compound of claim 2, wherein said somatostatin-based peptide further comprises -Ala-Gly-Cys-Lys-Asn-Phe- (SEQ ID NO:2).

5. The compound of claim 4, wherein -Ala-Gly-Cys-Lys-Asn-Phe- (SEQ ID NO:2) is comprised by the N-terminus of said somatostatin-based peptide.

6. The compound of claim 5, wherein said -Ala- residue of said somatostatin-based peptide is attached via said amino or thiol group NH or —S— group to (C-X).

7. The compound of claim 2, wherein said somatostatin-based peptide further comprises -Phe-Thr-Ser-Cys- (SEQ ID NO:3).

8. The compound of claim 7, wherein -Phe-Thr-Ser-Cys- (SEQ ID NO:3) is comprised by the C-terminus of said somatostatin-based peptide.

9. The compound of claim 2, wherein said somatostatin-based peptide further comprises -Ala-Gly-Cys-Lys-Asn-Phe- (SEQ ID NO: 2) and -Phe-Thr-Ser-Cys- (SEQ ID NO: 3).

10. The compound of claim 9, wherein said somatostatin-based peptide is somatostatin-14 or D-Trp$^8$-somatostatin-14.

11. The compound of claim 1, wherein said light-emitting moiety is selected from the group consisting of Bodipy, fluorescein, FTC, Texas red, phycoerythrin, rhodamine, carboxytetra-methylrhodamine, DAPI, indopyras dyes, Cascade blue, coumarins, NBD, Lucifer Yellow, propidium iodide, and derivatives thereof.

12. The compound of claim 1, wherein C-X is C=O or C=S =O or =S.

13. The compound of claim 1, wherein said compound is a pharmaceutically acceptable salt or complex thereof.

14. A method for labelling a receptor having an affinity for a somatostatin-based peptide by contacting said receptor with the compound of claim 1.

15. A compound of claim 1, wherein the number of amino acids in $R_2$ is between 7 and 14.

16. A compound of the formula:

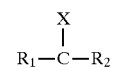

wherein $R_1$ is a light-emitting moiety;

$R_2$ is Y-Z-Q, wherein Z comprises -Phe-Phe-Trp-Lys-Thr- (SEQ ID NO:1) or -Phe-Phe-D-Trp-Lys-Thr-; each of Y and Q is an amino acid sequence such that the number of amino acids in $R_2$ is between 7 and 28; and CX is C=O, C=S, —CHOH, C=C=O, C=NH, —CH$_2$, —CHOR, —C=NR, —CHR, —CR$_3$R$_4$, wherein each of R, R$_4$, and R$_3$, independently, is H or a $C_1$–$C_6$ branched or unbranched, substituted or unsubstituted alkyl; and C of X-C is bonded via an —NH— or —S— group to an amino acid of $R_2$; and wherein said compound is selected from a mixture including said compound and secondary compounds having biological activities less than 0.25% of the biological activity of $R_2$—H in the presence of a receptor having affinity for somatostatin-based peptides.

17. The compound of claim 16, wherein said selection is accomplished by exposing said compound to a receptor recognizing a somatostatin-based peptide, and then selectively isolating said exposed compound if said compound exhibits substantial biological activity.

18. The compound of claim 17, wherein said compound having substantial biological activity is selected using high-pressure liquid chromatography.

19. The compound of claim 16, wherein $R_2$ is a somatostatin-based peptide.

20. The compound of claim 19, wherein said -Phe-Phe-Trp-Lys-Thr- (SEQ ID NO:1) or -Phe-Phe-D-Trp-Lys-Thr- is located at positions 7–11 of said somatostatin-based peptide.

21. A compound of claim 15, wherein the number of amino acids in $R_2$ is between 7 and 14.

* * * * *

UNITED STATES PATENT AND TRADEMARK OFFICE
CERTIFICATE OF CORRECTION

PATENT NO. : 5,824,772
DATED : October 20, 1998
INVENTORS : Jean-Pierre Vincent, Georges Gaudriault, and Alain Beaudet It is certified that error appears in the above-identified patent and that said Letters Patent is hereby corrected as shown below:

On the title page, item [73]
In the Assignee, replace "Advanced Bioconcept, Inc." with
--Advanced Bioconcept, Ltd.--;

In the Abstract, replace "or (SEQ ID NO: 1)" with
--(SEQ ID NO: 1) or--;

At Col. 1, line 5, replace "5,695,679" with --5,693,679-- ;

At Col. 7, line 18, replace "1mmole" with --1 mmole--;

At Col. 8, line 11, replace "rM" with --nM--;

At Col. 8, line 15, replace "sstr2 a" with --sstr2a--;

At Col. 8, line 51, replace "sstr2 a" with --sstr2a--;

At Claim 6, delete "amino or thiol group."

Signed and Sealed this

Twelfth Day of October, 1999

Attest:

Q. TODD DICKINSON

*Attesting Officer*   Acting Commissioner of Patents and Trademarks